United States Patent [19]

Ito

[11] Patent Number: 4,909,921

[45] Date of Patent: Mar. 20, 1990

[54] ELECTROCHEMICAL SENSOR FACILITATING REPEATED MEASUREMENT

[75] Inventor: Narushi Ito, Tokyo, Japan

[73] Assignee: NEC Corporation, Tokyo, Japan

[21] Appl. No.: 308,597

[22] Filed: Feb. 9, 1989

[30] Foreign Application Priority Data

Feb. 10, 1988 [JP] Japan .................................. 63-27476

[51] Int. Cl.$^4$ .............................................. C12M 1/40
[52] U.S. Cl. ..................................... 204/403; 357/25; 435/288; 435/291; 435/817
[58] Field of Search .................. 357/25; 435/288, 817, 435/291; 204/1 E, 403

[56] References Cited

U.S. PATENT DOCUMENTS

| | | | |
|---|---|---|---|
| 4,224,125 | 9/1980 | Nakamura | 204/403 |
| 4,490,216 | 12/1984 | McConnell | 204/1 T |
| 4,776,944 | 10/1988 | Janata et al. | 204/415 |
| 4,812,220 | 3/1989 | Iida et al. | 204/403 |

FOREIGN PATENT DOCUMENTS 59-209165 10/1984 Japan .
29658 2/1985 Japan .

OTHER PUBLICATIONS

"Biosensor Using the Semiconductor Technology", Miyahara et al., CPM 81-93, pp. 61-65, 68 and unnumbered page (1981).
"Integrated Enzyme FETS for Simultaneous Detections of Urea and Glucose", Miyahara et al., Sensors and Actuators, vol. 7, pp. 1-10, (1985).
"Collection of Prepared Papers for the 4th Study Meeting on Chemical Sensors", pp. 21 and 22, (1985).
Multi-Enzyme Electrode Using Hydrogen-Ion-Sensitive Field-Effect Transistors, Hanazato et al., IEEE Transactions on Electron Devices, vol. ED-33, No. 1, pp. 47-51, (Jan. 1986).
ph-Based Enzyme Potentiometric Sensors, Part 2, Glucose-Sensitive Field-Effect Transistor, Caras et al., Analytical Chemistry, vol. 57, No. 9, pp. 1920-1923, (Aug. 1985).
Glucose-Sensitive Field-Effect Transistor With a Membrane Containing Co-Immobilized Gluconolactonase and Glucose Oxidase, Hanazato, et al., Analytica Chimica Acta 212, pp. 49-59, a cover page having a date thereon of Sep. 15, 1988, (noted therein received Feb. 23, 1988).
ph-Based Enzyme Potentiometric Sensors, Part 3. Penicillin-Sensitive Field Effect Transistor, Caras et al., Analytical Chemistry, vol. 57, pp. 1924-1925, (1985).
Immobilized Enzyme Electrode Probes, Guilbault, understood to be from Solid Phase Biochemistry, John Wiley and Sons, N.Y., pp. 479-505, (1983).

*Primary Examiner*—G. L. Kaplan
*Attorney, Agent, or Firm*—Burns, Doane, Swecker & Mathis

[57] ABSTRACT

An electrochemical sensor wherein a FET for measuring chemical substances and a reference electrode are covered with a continuous hydrous polymer on an insulating substrate, and on the hydrous polymer, an enzyme-immobilized film is formed in a region positioned on a channel part of FET for measuring chemical substances.

8 Claims, 3 Drawing Sheets

ELECTROCHEMICAL SENSOR FACILITATING REPEATED MEASUREMENT

BACKGROUND OF THE INVENTION

1. Field of the Invention

The present invention relates to an electrochemical sensor for measuring the concentration of a chemical substance in a solution, and particularly to the structure of an electrochemical sensor of an FET (Field Effect Transistor) type.

2. Description of the Related Arts

As for semiconductor ion sensors for measuring the concentration of a specified organic substance in a solution, an ion sensitive field effect transistor (hereinafter called ISFET) biosensor wherein an enzyme-immobilized film is provided on the surface of a channel part of ISFET has been known heretofore as a kind of such sensors (Yuji Miyahara, Shoko Shiokawa, Toyoe Moriizumi, Hideaki Matsuoka, Isao Karube, and Syuichi Suzuki; "Biosensor using semiconductor technique", Denshi Tsushin Gakkai, Materials of Denshi Buhin Zairyo Kekyukai CPM 81-93, 61 (1981)). This ISFET biosensor is so designed that a change in the concentration of hydrogen ions in the enzyme-immobilized film, which is caused when the specified organic substance in the solution is decomposed in the film by the catalysis of enzyme, is detected from a change in the electroconductivity between the source and drain of ISFET, so as to measure the concentration of the specified organic substance. As examples of this enzyme-immobilized film having selectivity, an urease-immobilized film is known for detecting urea and a glucose-oxidase-immobilized film for detecting glucose, for instance (Sensors and Actuators, Vol. 7, pp. 1 to 10 (1985)).

Besides, an electrochemical sensor based on the principle that the enzyme-immobilized film is provided on a precious metal electrode formed on an insulating substrate and hydrogen peroxide produced by an enzyme reaction is measured by amperometry, has also been made public (Collection of Prepared Papers for the 4th Study Meeting on Chemical Sensors, pp. 21 and 22 (1985)).

A problem occurring when the electrochemical sensor is miniaturized to be put into practical use is that a reference electrode for giving a reference voltage to the enzyme-immobilized film through a solution to be measured can not be miniaturized. In order to avoid this problem, a means has been taken generally wherein a pseudo reference electrode and two FETs are formed on a single substrate and a differential output of the two FETs is measured. In other words, among the two FETs using the pseudo reference electrode commonly, one is constituted by ISFET wherein an enzyme electrode having the enzyme-immobilized film formed thereon is provided on a channel, and the other by differential reference FET wherein such an electrode as the above is not provided, so as to measure a difference between an output of the ISFET and an output of the differential reference FET, i.e. the so-called differential output. According to this method, an effect of drift or the like in various measuring solutions can be neglected, and only a change in a substance to be measured due to the enzyme reaction can be measured. Besides, the reference electrode can be miniaturized by using a metal or the like.

In the electrochemical sensor of this type, however, the electrical path between FETs and the pseudo reference electrode produced by the solution to be measured disappears completely outside the solution and an electrically open state is brought about, thus resulting in a variation in the sensitivity of the sensor on the occasion of replacement of the measuring solution or in similar cases. This produces problems that a reference value of an output of the sensor is shifted, a time is required until this reference value of the output is stabilized, etc.

Contemplated for solving prior-art problems as described above, the present invention has an object of furnishing an electrochemical sensor which enables the immediate attainment of a stable output even when the sensor is taken out of the measuring solution for replacement of the solution or the like and then put in it again.

SUMMARY OF THE INVENTION

The present invention enables the realization of the electrochemical sensor which has FET and a reference electrode adjacently on one substrate, both of these FET and reference electrode being covered with a continuous hydrous polymer, and an enzyme-immobilized film being formed on the hydrous polymer on a channel part of FET. This electrochemical sensor is so constructed preferably that it has two FETs on the same substrate, having the enzyme-immobilized film on the hydrous polymer on the channel part of one of said FETs and not having the enzyme-immobilized film on the hydrous polymer on the channel part of the other FET, so as to make these two FETs operate differentially.

According to the present invention, the stable electrochemical sensor can be realized wherein FETs and the reference electrode are made continuous to each other by the hydrous polymer, the water content remains as it is in the hydrous polymer on the sensor even when the sensor is separated from a solution to be measured and, therefore, a leakage current flowing through a measuring circuit at the time of measurement is left to flow therethrough until said water content dries up. Accordingly, neither an open-circuit nor shift of a reference value of an output of the measuring circuit occurs on the occasion of replacement of the solution to be measured or the like, and thus promoting elimination of such a problem as taking a time for this reference value of the output to be stabilized again.

BRIEF DESCRIPTION OF THE DRAWINGS

The above and further objects, features and advantages of the present invention will become more apparent from the following detailed description taken in conjunction with the accompanying drawings, wherein.

DESCRIPTION OF THE PREFERRED EMBODIMENT

Figure 1:
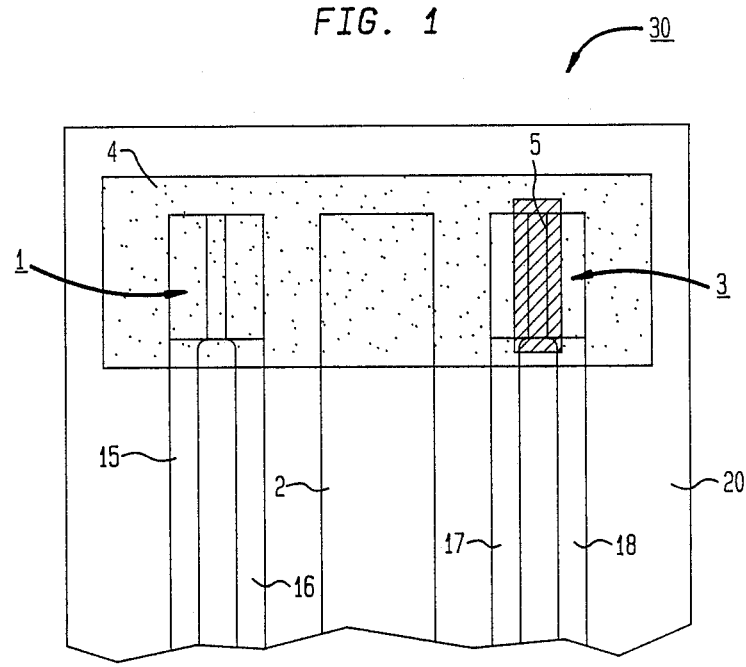
FIG. 1 is a schematical plan view of an electrochemical sensor according to one embodiment of the present invention.

Referring now to FIG. 1, it is found that an enzyme sensor 30 which is one embodiment of the present invention has a pseudo reference electrode 2 formed of gold and a pair of FETs, a reference ion-sensitive field effect transistor (REFET) 1 and an enzyme ion-sensitive field effect transistor (ENFET) 3 using the pseudo reference electrode 2 commonly, on a substrate 20 formed of sapphire. The pseudo reference electrode 2 and the paired FETs are covered with a continuous hydrous polymer film 4, and an enzyme-immobilized film 5 is formed on a channel part of ENFET 3. Both REFET 1 and ENFET 3 are thin-film MOSFETs each having a channel part formed of silicon, and source and drain electrodes 15 to 18 thereof are led out onto the substrate 20 by means of gold or the like. The hydrous polymer film 4 has albumin and a crosslinking agent as main constituents and a film thickness of 0.5 $\mu$m or below in the present embodiment. Agar, gelatin, alginic acid, K-carrageenan or the like can be alternatively used for the hydrous polymer film 4.

Parts among REFET 1, ENFET 3 and the pseudo reference electrode 2 of the sensor 30 are dipped in a solution to be measured, or the solution is dripped thereon. Then, the source electrodes 16 and 17 are connected commonly and a certain voltage such as an earthing voltage is applied thereto, while the drain electrodes 15 and 18 are connected to a power source through load resistances respectively. Then, a reference voltage is given to the pseudo reference electrode 2, and from a potential difference between the drain electrodes 15 and 18 at this time, the concentration of a specified chemical substance in the aforesaid solution is measured.

Since there is no hydrous polymer film covering REFET 1 and ENFET 3 and the foreend part of the pseudo reference electrode 2 commonly in the prior-art sensor, the electrical path between each FET and the pseudo reference electrode secured by the solution to be measured is broken when they are put outside the solution, on the occasion of the measurement of the chemical substance. According to the electrode structure of the present embodiment, in contrast, the connection between REFET 1 and the pseudo reference electrode 2 and that between the pseudo reference electrode 2 and ENFET 3 are kept in the same state as in the measurement even when the sensor 30 is taken out of the solution to be measured, and thus the circuit is not broken electrically. Therefore, there occurs no such problem as a reference value of an output of a measuring circuit is shifted or as it takes a time for the output to return to the original reference value and become stable.

Figure 2A:
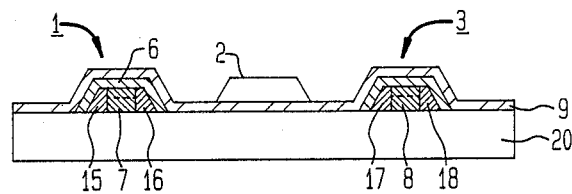
FIGS. 2(a) to 2(e) are sectional views showing sequential manufacturing processes of the electrochemical sensor according to the one embodiment of the present invention.

FIGS. 2(a) to 2(e) are sectional views showing a method of manufacturing the sensor shown in FIG. 1, in the sequence of processes. First, two FETs having no gate electrode (one is provided for REFET 1 and the other for ENFET 3) and the reference electrode 2 are formed on the sapphire substrate 20 as shown in FIG. 2(a). As for the two FETs, P-type silicon 7 and N-type silicon 8 are deposited as channel parts thereof, and the source and drain electrodes 15 to 18 of gold are formed on the opposite sides thereof respectively. Each channel part is made to have a gate length of 50 $\mu$m and a gate width of 350 $\mu$m. On the surfaces of these P-type silicon 7 and N-type silicon 8 and the foreend parts of the source and drain electrodes 15 to 18, a gate oxide film 6 of $SiO_2$ is formed. The surface of this film is covered entirely with a silicon nitride film 9, and the pseudo reference electrode 2 of gold is formed on a part of the silicon nitride film 9 located between the two FETs.

Figure 2B:
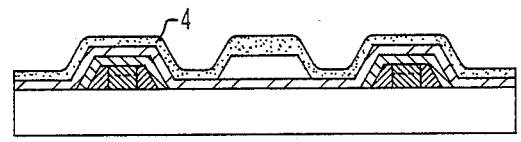
Figure 2C:
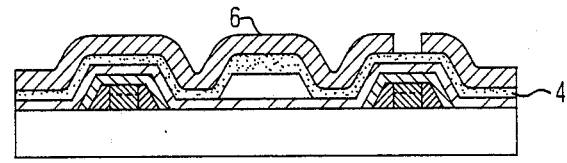
Figure 2D:
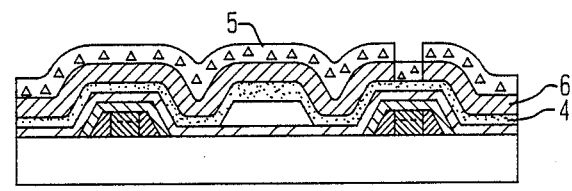
Figure 2E:
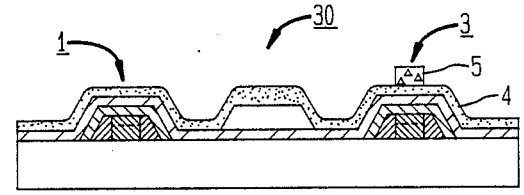

Next, the hydrous polymer film 4 is applied by coating on the whole surfaces of each FET and the pseudo reference electrode 2 as shown in FIG. 2(b), and, thereafter, a photoresist 6 is applied on the hydrous polymer film 4 as shown in FIG. 2(c), while an opening is formed on the channel part of one FET. Then, the enzyme-immobilized film 5 of glucose oxidase being 1 $\mu$m thick is formed by coating as shown in FIG. 2(d), and the photoresist 6 is removed by ultrasonic cleaning in acetone. Thereby the enzyme-immobilized film 5 is formed only on the channel part of one FET wherein the opening of the photoresist 6 is formed, and this part of the film is made to be ENFET 3, while the other FET is made to be REFET 1. The sensor 30 shown in FIG. 2(e) is obtained in this way.

Figure 3A:
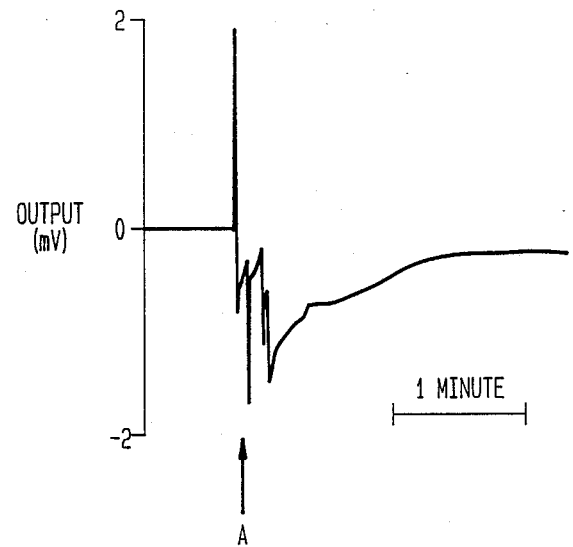
FIG. 3(a) is a graph showing a variation in an output of a prior-art electrochemical sensor at the time of replacement of a solution to be measured, and FIG. 3(b) a graph showing a variation in an output of the electrochemical sensor according to the one embodiment of the present invention at the time of replacement of the solution to be measured.
Figure 3B:
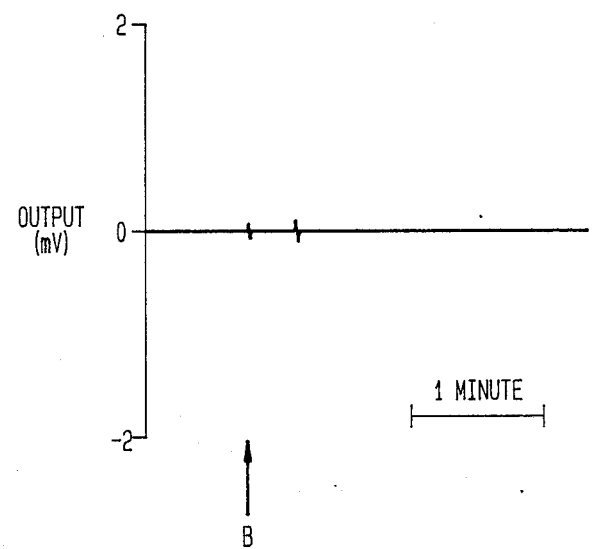

FIGS. 3(a) and 3(b) show a comparison in variation of an output on the occasion of replacement of the solution to be measured between the cases when a chemical substance is measured by using the sensor 30 of the present embodiment and when it is measured by using the prior-art sensor. FIG. 3(a) is a graph showing a variation in an output in the prior-art sensor on the occasion when the solution to be measured is replaced. The output turns to be unstable in the moment when the sensor is taken out of the solution for replacement of the solution (indicated by A in the figure). Even when the sensor is put in a fresh solution subsequently, a time of one minute or more is required until it becomes stable in the steady state of the original output. FIG. 3(b) shows the result of the replacement of the solution to be measured which is conducted in regard to the sensor 30 according to one embodiment of the present invention, in the same way as in FIG. 3(a). In the case of FIG. 3(b), the variation in the output does not occur almost at all and the steady state is maintained at the moment when the sensor 30 is taken out of the solution (indicated by B in the figure), although some spike-shaped variation in the output appears in the moment. When a subsequent measurement is conducted, accordingly, it is unnecessary to wait for the stabilization of the output in the steady state, and thus the measurement can be started immediately.

In the prior-art sensor, as described above, a leakage current caused by the solution to be measured between the reference electrode and each FET disappears on the occasion of replacement of the solution, and therefore there occurs the variation in the output, or it takes a time for the output to return to the steady state and become stable. In the sensor according to the present invention, in contrast, the leakage current caused by the solution to be measured between the reference electrode and each FET is maintained by the water content in the solution which is contained in the hydrous polymer, and therefore the sensor is free from such a shortcoming at the output is varied or as a time is needed until the output returns to the steady state and becomes stable, thus the stable electrochemical sensor being obtained.

The present invention is not limited to the above-described electrochemical sensor of the differential type, but the conductivity types of semiconductors of the respective channel regions of ENFET and REFET may also be identical, and the same effect can be produced by a device wherein one pseudo reference electrode and one ISFET having the enzyme-immobilized film on the channel are formed on the same insulative substrate.

What is claimed is:

1. An electrochemical sensor comprising:
   a substrate having an insulative surface;
   FET for measurement formed on said substrate and having a source, a drain, a channel portion and an enzyme-immobilized film disposed above said channel portion;
   a reference electrode formed adjacently to said FET for measurement on said substrate; and
   a hydrous polymer continuously covering said channel portion of said FET for measurement and said reference electrode.

2. An electrochemical sensor according to claim 1, wherein said hydrous polymer is constituted by a substance selected from a group consisting of albumin, agar, gelatin, alginic acid and K-carrageenan.

3. An electrochemical sensor according to claim 2, wherein said enzyme-immobilized film is formed on said hydrous polymer on said channel portion of said FET for measurement.

4. An electrochemical sensor according to claim 3, wherein a FET for comparison is further provided adjacently to said reference electrode on said substrate, said hydrous polymer being so formed as to cover said FET for comparison.

5. An electrochemical sensor according to claim 1, wherein said enzyme-immobilized film is formed on said hydrous polymer on said channel portion of said FET for measurement.

6. An electrochemical sensor having:
   an insulative substrate;
   a reference electrode formed on said insulative substrate;
   first and second semiconductor layers formed adjacently to said reference electrode on said insulative substrate;
   source and drain electrodes formed on the respective opposite sides of said first and second semiconductor layers;
   an insulating film covering the respective surfaces of said first and second semiconductor layers;
   a hydrous polymer covering said insulating film and said reference electrode commonly; and
   an enzyme-immobilized film formed selectively on said hydrous polymer on said first semiconductor layer.

7. An electrochemical sensor according to claim 6, wherein said hydrous polymer is constituted by a substance selected from a group consisting of albumin, agar, gelatin, alginic acid and K-carrageenan.

8. An electrochemical sensor according to claim 7, wherein said first and second semiconductor layers are different in a conductivity type from each other.

* * * * *